(12) United States Patent
Cukrowski

(10) Patent No.: US 8,722,666 B2
(45) Date of Patent: May 13, 2014

(54) SEDATIVE FOR USE DURING EYE SURGERY

(71) Applicant: Walter J. Cukrowski, Birmingham, MI (US)

(72) Inventor: Walter J. Cukrowski, Birmingham, MI (US)

( * ) Notice: Subject to any disclaimer, the term of this patent is extended or adjusted under 35 U.S.C. 154(b) by 0 days.

(21) Appl. No.: 13/971,970

(22) Filed: Aug. 21, 2013

(65) Prior Publication Data

US 2013/0338149 A1 Dec. 19, 2013

Related U.S. Application Data

(62) Division of application No. 12/858,475, filed on Aug. 18, 2010, now abandoned.

(60) Provisional application No. 61/235,470, filed on Aug. 20, 2009.

(51) Int. Cl.
*A61K 31/465* (2006.01)

(52) U.S. Cl.
USPC .......................................... 514/220; 514/912

(58) Field of Classification Search
USPC ................................................ 514/220, 912
See application file for complete search history.

(56) References Cited

U.S. PATENT DOCUMENTS

2004/0102440 A1    5/2004   Wong

*Primary Examiner* — Zohreh Fay
(74) *Attorney, Agent, or Firm* — Gifford, Krass, Sprinkle, Anderson & Citkowski, P.C.

(57) ABSTRACT

A drug for sedating a patient, and especially a smoker, during eye surgery. The drug includes a sedative such as midazolam in a mix with nicotine. The mixture is injected into the patient prior to the eye surgery.

3 Claims, 1 Drawing Sheet

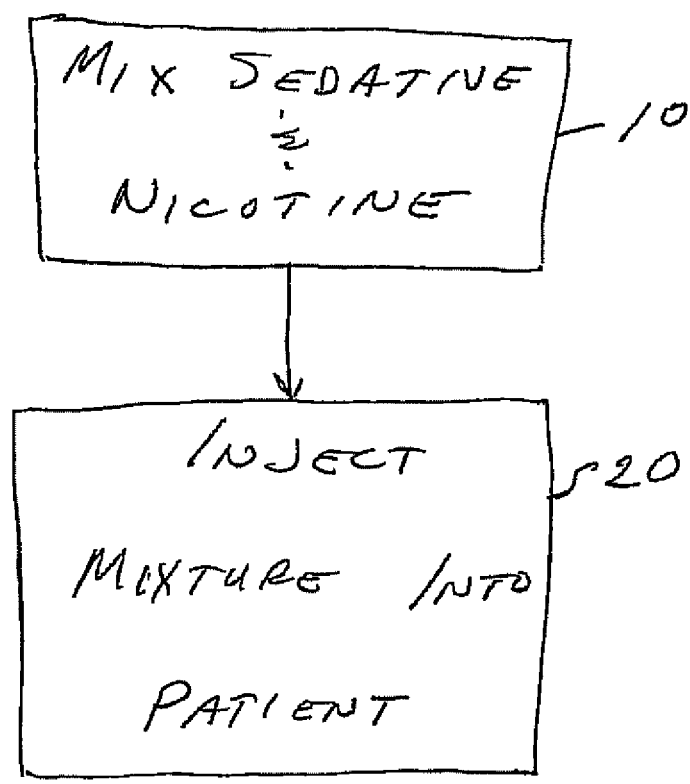

SEDATIVE FOR USE DURING EYE SURGERY

CROSS REFERENCE TO RELATED APPLICATIONS

This application is a division of U.S. patent application Ser. No. 12/858,475 filed Aug. 18, 2010, which claims priority of U.S. Provisional Patent Application Ser. No. 61/235,470 filed Aug. 20, 2009, which is incorporated herein by reference.

BACKGROUND OF THE INVENTION

I. Field of the Invention

The present invention relates generally to pharmaceuticals and, more particularly, to an intravenous drug for use prior to eye surgery.

II. Description of Related Art

Eye surgery for the removal of cataracts and the subsequent implantation of an artificial lens after the cataract has been removed has become an increasingly common surgical procedure. During such procedure, it is necessary that the patient and his or her eye remain perfectly still to allow the proper insertion not only of the surgical tools, but also the artificial lens, during the eye surgery.

Typically, the patient is mildly sedated with a sedative, such as midazolam, which is sold under the trademark Versed®. For many people, sedation by midazolam together with freezing the eye is sufficient to render the eye sufficiently stable permit the surgical procedure.

Smokers, and particularly heavy smokers, however, have presented a new challenge to eye surgery involving the removal of cataracts and the subsequent implantation of the artificial lens. It has been discovered that when such patients are sedated by a sedative, such as midazolam, alone, the patient nevertheless fidgets and twitches during the eye surgery. When this occurs, it is necessary to use other medical procedures to completely sedate the patient and completely prevent the movement of the patient's eye during the surgical procedure. These other medical procedures, however, disadvantageously pose greater surgical risk, even the loss of eyesight, for the patient as opposed to a simple intravenous injection of a sedative.

SUMMARY OF THE PRESENT INVENTION

The present invention provides a drug which overcomes all of the above-mentioned disadvantages of the previously known drugs.

In brief, in the present invention a sedative, such as midazolam, is mixed with nicotine to form an injectable dose. The ratio of sedative to nicotine ranges from 2:1 to 1:2.

Prior to the eye surgery, the mixture of the sedative and nicotine is injected into the patient in the standard fashion. It has been found, however, that the addition of the nicotine to the sedative reduces twitching and fidgeting of patients who are smokers and particularly patients who are heavy smokers.

BRIEF DESCRIPTION OF THE DRAWING

A better understanding of the present invention will be had upon reference to the following detailed description when read in conjunction with the accompanying drawing in which the single FIGURE is a flowchart illustrating the method of the present invention.

DETAILED DESCRIPTION OF A PREFERRED EMBODIMENT OF THE PRESENT INVENTION

With reference to the drawing, prior to eye surgery of a patient, and especially a patient who is a heavy smoker, a sedative and nicotine are intermixed at step 10. Both the sedative and the nicotine are in liquid form.

Preferably, the sedative comprises midazolam although other sedatives may alternatively be used without deviation from the scope or spirit of the invention. Furthermore, the ratio of sedative to nicotine in the mixture ranges between 2:1 to 1:2 by volume.

After the mixture is formed in step 10, the mixture is injected into the patient at step 20. In practice, it has been discovered that the addition of the nicotine to the sedative reduces twitching and fidgeting by the patient, particularly when the patient is a heavy smoker. This, in turn, allows the doctor to perform the eye surgery without the need to perform higher risk medical procedures on the patient prior to the eye surgery.

Having described my invention, however, many modifications thereto will become apparent to those skilled in the art to which it pertains without deviation from the spirit of the invention as defined by the scope of the appended claims.

I claim:

1. A method of sedating a patient prior to eye surgery comprising the steps of:

mixing a sedative and nicotine together to form a mixture, and injecting said mixture into a patient in need of eye surgery, prior to said eye surgery.

2. The method of claim 1 wherein said sedative comprises midazolam.

3. The method of claim 1 wherein the ratio of sedative to nicotine by volume is in the range of 2:1 to 1:2.

* * * * *